United States Patent [19]

Battey et al.

[11] 4,242,523

[45] Dec. 30, 1980

[54] PROCESS FOR THE PREPARATION OF PARA-NITROSO-DIPHENYL-HYDROXYLA-MINES

[75] Inventors: Paul K. Battey, Ormskirk, England; Manfred Bergfeld, Erlenbach, Fed. Rep. of Germany; Peter Hope, Liverpool, England

[73] Assignee: Akzona Incorporated, Asheville, N.C.

[21] Appl. No.: 67,784

[22] Filed: Aug. 20, 1979

[30] Foreign Application Priority Data

Aug. 18, 1978 [GB] United Kingdom ............... 33790/78

[51] Int. Cl.³ .................... C07C 79/46; C07C 85/24; C07C 101/72
[52] U.S. Cl. ...................................... 560/48; 560/21; 560/45; 560/46; 560/47; 564/300
[58] Field of Search ................. 260/576, 571; 560/48, 560/27, 21

[56] References Cited

U.S. PATENT DOCUMENTS

| | | | |
|---|---|---|---|
| 3,933,848 | 1/1976 | Feinstein et al. | 260/576 X |
| 4,129,740 | 12/1978 | Zengel et al. | 260/571 X |

FOREIGN PATENT DOCUMENTS

| | | | |
|---|---|---|---|
| 1147237 | 4/1963 | Fed. Rep. of Germany | 260/576 |
| 2020043 | 10/1970 | Fed. Rep. of Germany | 260/576 |

OTHER PUBLICATIONS

Boyer, "J. Org. Chem.", vol. 24, p. 2038 (1959).
Bamberger et al., "Berichte", vol. 31, pp. 1513–1522 (1898).

*Primary Examiner*—John Doll
*Attorney, Agent, or Firm*—Francis W. Young; Robert F. Green

[57] ABSTRACT

An improved process for the preparation of para-nitroso-diphenyl-hydroxylamines is discussed. In the improved process the dimerizing rearrangement of a nitroso benzene is performed in the presence of at least 0.5 mole of a Lewis acid per mole of nitroso compound.

9 Claims, No Drawings

PROCESS FOR THE PREPARATION OF PARA-NITROSO-DIPHENYL-HYDROXYLAMINES

BACKGROUND OF THE INVENTION

This invention relates to a process for the preparation of para-nitroso-diphenyl-hydroxylamines.

Para-nitroso-diphenyl-hydroxylamines may be obtained by the dimerization of nitroso benzenes in concentrated sulphuric acid (E. Bamberger et al., B. 31, page 1513 (1898)). Since the process is highly exothermic, relatively large quantities of concentrated sulfuric acid must be used to achieve adequate mixing of the components and dissipation of heat. Ice or water must be added to the mixture to isolate the reaction product and the large quantities of dilute sulphuric acid which are thus formed are neutralized and subsequently removed as effluent. The recovery of the sulphuric acid is not economically practical, partly because it is contaminated with nitrogen-containing organic material. The process is therefore not suitable for the industrial manufacture of para-nitroso-diphenyl-hydroxylamines.

In the process described in German Patent No. 2,020,043, the dimerizing rearrangement of nitroso benzenes is performed with a sulphuric acid having a concentration of at least 50%, by weight, preferably at least 75%, by weight, in the presence of an organic liquid, such an aliphatic hydrocarbon, a halogenated hydrocarbon, or an aromatic nitro compound, at temperatures of from about 5 to about 50° C. Since the reaction product decomposes very rapidly in the strongly acetic solution at higher temperatures, the heat of reaction must be rapidly removed. Such removal is performed by the organic liquid, but, in such a process, the sulphuric acid must also be used in large excess, namely in up to 10 times, preferably 2.5 to 6.5 times, the molar quantity of nitroso benzene. The foregoing again gives rise to the disadvantages already described with respect to the process of Bamberger et al. Moreover, the reaction product which is obtained is of poor quality since it contains significant quantities of tarry constituents in addition to products which are sulphonated in the nucleus. When stoichiometric quantities of sulphuric acid are used, para-nitroso-diphenyl-hydroxylamine precipitates in the form of its sulphate, as a viscous, dark mass which is technically difficult to handle and also contains substantial quantities of tar, in addition to products which are sulphonated in the nucleus.

In the process described in German Patent No. 1,147,237, hydrogen fluoride is used as a dimerizing agent instead of concentrated sulphuric acid. The reaction is performed at temperatures between −20° C. and 50° C., optionally in the presence of an inert organic solvent (see K. Wiechert et al, Z. Chem. 15 (1955) page 21). In such a process the dimerizing agent is also used in a large excess because hydrogen fluoride serves not only as the catalyst but also as the solvent. If hydrogen fluoride is used in the stoichiometric amount, a yield of only 25% of theoretical is obtained and the product is contaminated with derivatives which are fluorinated in the nucleus. The hydrogen fluoride is distilled off under vacuum after the reaction and may be recycled. However, hydrogen fluoride has the disadvantage of having a low boiling point and a very pungent odor. Furthermore, its vapors are highly toxic to the respiratory system. Moreover, the desired product is obtained as a viscous mass which is still contaminated with about 10 to about 20% of hydrogen fluoride adhering to it. The hydrogen fluoride is virtually impossible to recover because under the necessary conditions para-nitroso-diphenyl-hydroxyl-ammonium fluorides decompose to a blackish brown mass. The wash water is therefore also contaminated with hydrogen fluoride and problems of corrosion also occur. The process, therefore, is very expensive with respect to the apparatus required, so that it is not truly suitable for the preparation of para-nitroso-diphenyl-hydroxylamines on an industrial scale.

It is also known that para-nitroso-diphenyl-hydroxylamine is formed together with nitrobenzene when nitrosobenzene is treated with peroxy trifluoro acetic acid (J. H. Beyer, J. Org. Chem. 24, 2038 (1959)). In such a process, peroxytrifluoro acetic acid oxidizes nitrosobenzene to form nitrobenzene and concurrently catalyzes the dimerization of nitrosobenzene to para-nitroso-diphenyl-hydroxylamine. The formation of nitrosobenzene is favored at higher temperatures and the formation of para-nitroso-diphenyl-hydroxylamine at lower temperatures. In the most favorable instances, the quantity of para-nitroso-diphenyl-hydroxylamine obtained is 35% of theoretical. The process is therefore not very selective and again is unsuitable for the commercial production of para-nitroso-diphenyl-hydroxylamines.

In German Patent No. 2,703,919 (U.S. Pat. No. 4,129,740) a process is described for the preparation of para-nitroso-diphenyl-hydroxylamines by the reaction of a nitroso compound of the benzene series by itself or with another such compound, in the presence of an acid, as a catalyst. The process is characterized in that an aliphatic, cycloaliphatic or aromatic sulphonic acid having a $pK_a$ value<1, perchloric acid or trifluoro acetic acid is used as the catalyst in a quantity of at least 0.5 mole per mole of nitroso compound(s), and the reaction is performed at a temperature of from about −20° C. to about 60 C.

SUMMARY OF THE INVENTION

According to the present invention there is provided an improved process for the preparation of para-nitroso-diphenyl-hydroxylamines by the dimerizing rearrangement of one or more nitroso compounds of the benzene series. In the improved process the catalyst for the dimerizing rearrangement is a Lewis acid which is utilized in an amount of at least 0.5 mole per mole of nitroso compound(s).

Thus, the present invention provides an improved process in which one member selected from the group consisting of nitroso-benzene, ortho-substituted nitrosobenzenes, meta-substituted nitrosobenzenes, ortho-meta-disubstituted nitrosobenzenes, and para-substituted nitrosobenzenses, is reacted with one member selected from the group consisting of nitrosobenzene, ortho-substituted nitrosobenzenes, meta-substituted nitrosobenzenes, and ortho-meta-disubstituted nitrosobenzenes, in the presence of an acid catalyst. The improvement comprises utilizing as the acid catalyst a Lewis acid in an amount equal to or greater than 0.5 mol of acid per mol of nitroso reactants at a temperature from about −20° C. to about 60° C.

DETAILED DESCRIPTION OF THE PREFERRED EMBODIMENTS

The Lewis acid used in accordance with the present invention is any substance, except a proton, which can take up an electron pair to form a covalent bond. Examples of useful Lewis acids include halides of zinc, boron, titanium, tin, antimony, iron, aluminium and manganese.

Especially useful, and thus preferred, are boron trifluoride and its commonly used complexes with, for example, ether, methanol, and acetic acid. Another very useful and thus preferred combination is that of ferric chloride together with a carboxylic acid, such as formic or acetic acid. The ferric chloride and the carboxylic acid are generally used in a ratio of at least 1.0 mole of ferric chloride and 1.0 mole of the carboxylic acid per mole of the nitroso compound.

The process according to the present invention is particularly suitable for the preparation of para-nitroso-diphenyl-hydroxylamine by the dimerizing rearrangement of nitrosobenzene. However, the process is also suitable for the preparation of asymmetrically substituted para-nitroso-diphenyl-hydroxylamines which are obtained by the dimerizing rearrangement of ortho- or meta-substituted nitrosobenzenes, or through the reaction of a para-substituted nitrosobenzene with a nitrosobenzene which is unsubstituted in the para position. The starting compounds may be any nitroso compounds of the benzene series whose substituents are inert toward the catalyst. Examples of such substituents include nitro, alkoxy, haloalkyl, and carbalkoxy groups. The nitroso compounds may be substituted with one or more substituents. Thus, the term "substituted" when used throughout this application and in the appended claims means "substituted with any substituent which behaves in an inert manner with regard to catalysts utilized in the process of the present invention".

The ortho-substituted nitrosobenzenes used in the practice of the present process contain at least one ortho-substituent, but in addition thereto, may contain a second substituent in the other ortho-position. The meta-substituted nitrosobenzenes used in the practice of the present invention contain at least one meta-substituent, but in addition thereto, may contain a second substituent in the other meta-position. The para-substituted nitrosobenzenes used in the practice of the present invention may contain a second substituent in either of the ortho- or meta-positions, in addition to the substituent in the para-position. The ortho-meta-disubstituted nitrosobenzenes contain a substituent in either of the ortho-positions and a substituent in either of the para-positions.

The following substituted nitrosobenzene compounds are preferred: ortho-nitrosotoluene, ortho-chloro-nitrosobenzene, meta-chloro-nitrosobenzene, ortho-methoxy-nitrosobenzene, ortho-nitro-nitrosobenzene, meta-trifluoromethyl-nitrosobenzene, 2,6-dichloro-nitrosobenzene, 2,6-dimethyl-nitrosobenzene, meta-fluoro-nitrosobenzene, ortho-meta-nitrosobenzene, 2,5-dichloro-nitrosobenzene, meta-nitro-nitrosobenzene, and 2-nitroso-benzoic acid methyl ester. Mixtures of two or more of the above mentioned starting nitrosobenzene compounds may, of course, be used.

The process of the present invention is attractive from a technical and commercial viewpoint because (a) use is made of economical inorganic catalyst which are easy to separate from the organic phase, (b) the use of preferred Lewis acid catalysts shows little tendency toward by-product formation, and (c) the process may be performed under a wide variety of temperature/time conditions.

The quantity of catalyst to be used depends to a certain extent on the nature of the Lewis acid, but for obtaining high yields it is preferred to use the catalyst in at least the stoichiometric ratio, thus in quantities corresponding to at least 0.5 mole per mole of nitroso compounds. Generally, the amount of catalyst utilized will be from about 0.5 to about 10 moles per mole of nitroso compound, but it is a particular advantage of the catalyst according to the present invention that they may be used in smaller quantities than the conventional acids, thus preferably in quantities from 0.5 to 1.0 mole per mole of nitroso compound. The foregoing results in not only economical advantages, but also considerably facilitates the final processing of the reaction mixture.

The process of the present invention may be optionally performed in the presence of an organic solvent. If an organic solvent is used, it is not absolutely necessary to operate in the homogeneous phase, but both the nitroso compound and the catalyst should be at least partly soluble in the solvent. It is also desirable for the resulting salt of the para-nitroso-diphenyl-hydroxylamine to be soluble in the solvent because the reaction product can then be obtained in a pure form. Suitable organic solvents include aliphatic, cycloaliphatic, and aromatic hydrocarbons and they may carry one or more alkyl, halogen and/or nitro groups. The solvents which are preferred in the present process are nitromethane, nitrobenzene, methylenechloride, chloroform, 1,2-dichloroethane, 1,1,1-trichloromethane, and 1,1,2,2-tetrachloroethane.

The process of the present invention is typically performed at temperatures from about $-20°$ C. to about 60° C., preferably from about 20° C. to about 40° C. The reaction is strongly exothermic and therefore requires careful cooling of the reaction mixture, even when no solvent is utilized.

The process of the present invention may be suitably performed by introducing a solution or suspension of the nitroso compound(s) in an organic solvent into the reaction vessel and subsequently adding the catalyst portion-wise with vigorous stirring and with cooling. It is advantageous to carry out the reaction in a low boiling solvent, such as methylene chloride, under relux. In such a case, the heat of reaction is easily removed by cooling due to evaporation.

The para-nitroso-diphenyl-hydroxylamines are obtained in a highly pure state by the process of the present invention but, if necessary, they may be further purified in accordance with known procedures, for example, for recrystallization or reprecipitation. The foregoing may be formed by first dissolving the crude product in an aqueous alkali metal or alkaline earth metal hydroxide or in sodium sulphite and then re-precipitating it by the addition of a mineral acid.

Para-nitroso-diphenyl-hydroxylamines are valuable compounds which may be subsequently processed, for example, into antioxidants, antiozonants, or dyes. They are especially valuable as intermediates in the manufacture of para-phenylene-diamine antidegradants which are widely used in the rubber industry.

The present invention will be further described by the following non-limiting examples.

EXAMPLE 1

Nitrosobenzene (0.025 m, 2.68 g) was dissolved in methylene dichloride (6 cc) and a solution of boron trifluoride etherate (0.0275 m, 3.91 g) in methylene dichloride (4 cc) added rapidly to the stirred green colored solution. A mildly exothermic reaction ensued resulting in gentle reflux of the methylene dichloride and the formation of a dark red/brown solution. After a further period of 15 minutes stirring, this solution was added to distilled water (75 cc) in a 1 liter vessel and the methylene dichloride distilled out under water pump vacuum on a rotary evaporator (35° C./approximately 20 mm Hg). The precipitated N-phenyl-(4-nitrosophenyl)-hydroxylamine was filtered off, washed with ice-cold water (3×10 cc) and dried (50° C./1 mm Hg) to constant weight.

Yield=2.56 (96%) of a fine brown powder.

EXAMPLE 2

Nitrosobenzene (0.025 m, 2.68 g) was dissolved in methylene dichloride (6 cc) and a solution of boron trifluoride etherate (0.0138 m, 1.96 g) in methylene dichloride (4 cc) added rapidly to the stirred green colored solution. A mildly exothermic reaction ensued, causing the methylene dichloride to reflux very gently and resulted in a dark red/brown solution. After a further period of 15 minutes stirring this solution was added to distilled water (75 cc) in a liter vessel and the methylene dichloride distilled out under water pump vacuum on a rotary evaporator (35° C./approximately 20 mm Hg). The precipitated N-phenyl-(4-nitrosophenyl)-hydroxylamine was filtered off, washed with ice-cold water (3×10 cc) and dried (50° C./1 mm Hg) to constant weight.

Yield=2.47 g (92%) of a fine orange/brown solid.

EXAMPLE 3

Nitrosobenzene (0.025 m, 2.68 g) was partially dissolved in methylene dichloride (10 cc) and anhydrous ferric chloride (0.05 m, 8.2 g) added in a single portion. A vigorously exothermic reaction ensued causing the methylene dichloride to reflux and giving rise to an orange/brown solution and dark tarry material. Examination of the tar (in MeOH solution) and the methylene dichloride solution by UV indicated that most of the starting material/product is located in the tar and of this material approximately 20% was the dimer. Further stirring resulted in no further dimerization but refluxing for 5 hours resulted in total consumption of nitrosobenzene. The methylene dichloride was evaporated off and the residual dark tarry residue extracted with 10% sodium hydroxide solution. A brown solid was filtered off and the resultant red solution acidified with concentrated hydrochloric acid when a brown solid precipitated. This material was filtered off, washed with ice-cold water until the washings were neutral, and dried to constant weight (50° C./1 mm Hg).

Yield=1.16 g (43%).

EXAMPLE 4

Nitrosobenzene (0.025 m, 2.68 g) and anhydrous ferric chloride (0.025 m, 4.05 g) were mixed and stirred while a solution of formic acid (0.025 m, 1.15 g) in methylene dichloride (10 cc) was added rapidly. An exothermic reaction ensued which caused the methylene dichloride to reflux and resulted in a deep orange/brown solution and orange/brown tar. After stirring for a further 15 minutes the total reaction mixture was dissolved in methanol. Quantitative UV indicates a quantitative conversion to N-phenyl-(4-nitrosophenyl)-hydroxylamine.

What is claimed is:

1. In a process for the preparation of para-nitrosodiphenyl-hydroxylamines wherein one member selected from the group consisting of nitrosobenzene, ortho-substituted nitrosobenzenes, meta-substituted nitrosobenzenes, ortho-meta-disubstituted nitrosobenzenes, and para-substituted nitrosobenzenes, is reacted with one member selected from the group consisting of nitrosobenzenes, ortho-substituted nitrosobenzenes, meta-substituted nitrosobenzenes, and ortho-meta-disubstituted nitrosobenzenes in the presence of an acid catalyst, the improvement comprising utilizing as the acid catalyst a Lewis acid, in an amount equal to or greater than 0.5 mol of acid per mol of nitroso reactants, and performing the reaction at a temperature from about −20° C. to about 60° C.

2. In the process of claim 1, the improvement wherein the Lewis acid is boron trifluoride or a complex thereof.

3. In the process of claim 1, the improvement wherein the Lewis acid is a complex of boron trifluoride with ether, methanol, or acetic acid.

4. In the process of claim 1, the improvement wherein the Lewis acid is ferric chloride and is used in combination with a carboxylic acid.

5. In the process of claim 4, the improvement wherein the carboxylic acid is formic or acetic acid.

6. In the process of claim 4 or 5, the improvement wherein at least 1.0 mol of ferric chloride and at least 1.0 mole of carboxylic acid are used per mole of nitroso reactants.

7. In the process of claim 1, 2, 3, 4, or 5, the improvement wherein the reaction is performed at a temperature from about 20° to about 40° C.

8. In the process of claim 7, the improvement wherein the reaction is performed by adding the catalyst portion-wise to a solution or suspension of the nitroso reactants in an organic solvent, with cooling and vigorous stirring.

9. In the process of claim 8, the improvement wherein the organic solvent is methylene chloride and the reaction is performed under reflux.

* * * * *